US006221382B1

United States Patent
Ishida et al.

(10) Patent No.: US 6,221,382 B1
(45) Date of Patent: *Apr. 24, 2001

(54) SHEET PACK

(75) Inventors: Koichi Ishida, Tokyo; Manabu Kaneda; Yasuhiro Komori, both of Tochigi, all of (JP)

(73) Assignee: Kao Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/451,083

(22) Filed: Nov. 30, 1999

Related U.S. Application Data

(63) Continuation of application No. 08/817,648, filed on Sep. 26, 1997, now Pat. No. 6,042,844, and a continuation of application No. PCT/JP97/00631, filed on Feb. 28, 1997.

(30) Foreign Application Priority Data

Mar. 4, 1996 (JP) ........................................ 8-75153

(51) Int. Cl.⁷ ..................................................... A61F 13/02
(52) U.S. Cl. ........................ 424/443; 424/446; 424/78.03; 424/78.37; 424/487; 514/844; 514/847; 514/944
(58) Field of Search ................................ 424/448, 78.02, 424/78.03, 78.08, 78.37, 484, 486, 487, 443, 446; 514/844, 847, 944

(56) References Cited

U.S. PATENT DOCUMENTS 4,839,345   6/1989  Doi et al. .
5,025,662   6/1991  Gueret et al. .
5,725,874   3/1998  Oda et al. .

FOREIGN PATENT DOCUMENTS

| 0 063 875 | 11/1982 | (EP) . |
| 0 309 309 | 3/1989 | (EP) . |
| 0 514 760 | 11/1992 | (EP) . |
| 3 648 247 | 6/1984 | (FR) . |
| 58-180408 | 10/1983 | (JP) . |
| 58-216109 | 12/1983 | (JP) . |
| 60-165902 | 8/1985 | (JP) . |
| 2-145505 | 6/1990 | (JP) . |
| 5-194180 | 8/1993 | (JP) . |
| 6-48917 | 2/1994 | (JP) . |
| 6-65048 | 3/1994 | (JP) . |
| WO 96/14822 | 5/1996 | (WO) . |

OTHER PUBLICATIONS

PCT Written Opinion.
PCT International Preliminary Examination Report.

Primary Examiner—S. Mark Clardy
Assistant Examiner—Michael A. Williamson
(74) Attorney, Agent, or Firm—Oblon, Spivak, McClelland, Maier & Neustadt, P.C.

(57) ABSTRACT

A sheet pack having a multi-layer moisture-permeable support including a hydrophobic layer and a hydrophilic layer, and a cosmetic substance, and a method for applying the sheet pack, including the steps of supplying moisture to skin and applying the sheet pack to the moisture-supplied skin.

14 Claims, 6 Drawing Sheets

SHEET PACK

This application is a Continuation of application Ser. No. 08/817,648 filed on Sep. 26, 1997 now U.S. Pat. No. 6,042,844; and International Application No. PCT/JP97/00631, filed on Feb. 28, 1997.

TECHNICAL FIELD

The present invention relates to a peel-off-type sheet pack.

BACKGROUND ART

A peel-off-type pack is a film-forming cosmetic article, which is applied to skin, left for a certain period of time to form a film, and then peeled off the skin.

The peel-off-type pack typically supplies moisture itself and moisture-retaining ingredients to the stratum corneum of the skin, while absorbing sebum from the skin. The peel-off-type pack forms a film on the skin to give appropriate tension to the skin and improve the blood circulation. When the peel-off-type pack is peeled off the skin, the peel-off-type pack removes dirt and keratotic plug of the skin.

The peel-off-type pack accordingly exhibits high emollient effects and excellent cleaning effects.

Known peel-off-type packs are in jelly-like, paste-like, or powdery form. Among the known peel-off-type packs, jelly-like and paste-like packs are directly applied to the skin to form a film and then peeled off the skin. The powdery pack is previously mixed with a liquid such as water, applied to the skin to form a film, and then peeled off the skin.

In any of the conventional peel-off-type packs, the cosmetic substance which forms the pack is generally applied to the skin with fingers. This application process inevitably causes some amount of the cosmetic substance to remain on the fingers, thereby wasting the cosmetic substance and staining the fingers. Another problem is difficulty in uniformly applying the pack to the surface of the skin.

Moreover, a relatively long period of time is required to complete the formation of a film after the application of the pack to the skin. This makes the skin treatment with a pack rather troublesome.

Standard amount of usage often gives an insufficient tensile strength to a resulting pack film, which may be torn in the course of peeling off and remain on the surface of the skin. In order to prevent the film from undesirably remaining on the skin, it is effective to use a greater amount of the pack to form a thicker film. This, however, further lengthens the period of time required for completing the formation of a film after the application of the pack to the skin.

A variety of sheet packs have recently been proposed to solve the above problems. One group is water-containing sheet packs mainly composed of a water-soluble polymer and water; for example, a sheet pack obtained by spreading a water-containing crosslinked gel made of polyacrylates and a crosslinking agent on a non-woven fabric as disclosed in Japanese Patent Laid-Open No. 58-180408, a water-containing sheet pack made of alginic acid, a water-soluble polymer and a crosslinking agent as essential components as disclosed in Japanese Patent Laid-Open No. 2-145505, and a face-coating mask sheet having plural layers the top surface of which being protected by a release sheet (plastic liner) and containing different cosmetic components in the respective layers as disclosed in Japanese Patent Laid-Open No. 6-48917.

Another group is dry sheet packs obtained by spreading and drying a thin film of a film-forming paste-like cosmetic substance, which includes a water-soluble polymer and water as main components; for example, a dry film-like cosmetic article mainly composed of a water-soluble polymer including medical or cosmetic components such as ascorbic acid as disclosed in Japanese Patent Laid-Open No. 58-216109, a cosmetic pack having a dry thin layer of a paste such as sodium polyacrylate or a dispersed layer of fine paste powder on one surface of a film as disclosed in Japanese Patent Laid-Open No. 60-165902, a sheet pack containing a polymer which is soluble in or swelled with both water and a non-aqueous solvent, and a polymer which is soluble in or swelled with only a non-aqueous solvent as essential components as disclosed in Japanese Patent Laid-Open No. 3-294213, a sheet pack cosmetic article including polyvinyl alcohol, the other polymer and a polyhydric alcohol as disclosed in Japanese Patent Laid-Open No. 5-194180, and a film pack having a water content of not higher than 25% by weight, containing sodium alginate and a polyhydric alcohol as disclosed in Japanese Patent Laid-Open No. 6-65048. Before their application, water or clear lotion is added to the dry sheet packs.

Those proposed sheet packs can be handled more easily than the conventional packs, but still have some drawbacks, such as sticky surface during its use, unintentional tear of the film in the course of peeling off, and remains of the film on the surface of the skin, therefore are not satisfactory. Also, there arises a problem in the sheet packs that a relatively long period of time is necessitated for completing the formation of a film.

An object of the present invention is to provide an improved peel-off-type pack which does not have a sticky surface, completes the formation of a film in a relatively short period of time, is not easily torn in the course of peeling off, and does not cause the remains of the film on the surface of the skin.

These and other objects of the present invention will be apparent from the following description.

DISCLOSURE OF THE INVENTION

In accordance with the present invention, there is provided a sheet pack comprising a multi-layer moisture-permeable support having a hydrophobic layer and a hydrophilic layer, and a cosmetic substance.

Also, in accordance with the present invention, there is provided a method for applying the above sheet pack to skin, comprising (A) supplying moisture to skin, and (B) applying the sheet pack to the moisture-supplied skin.

BEST MODE FOR CARRYING OUT THE INVENTION

Figure 1:
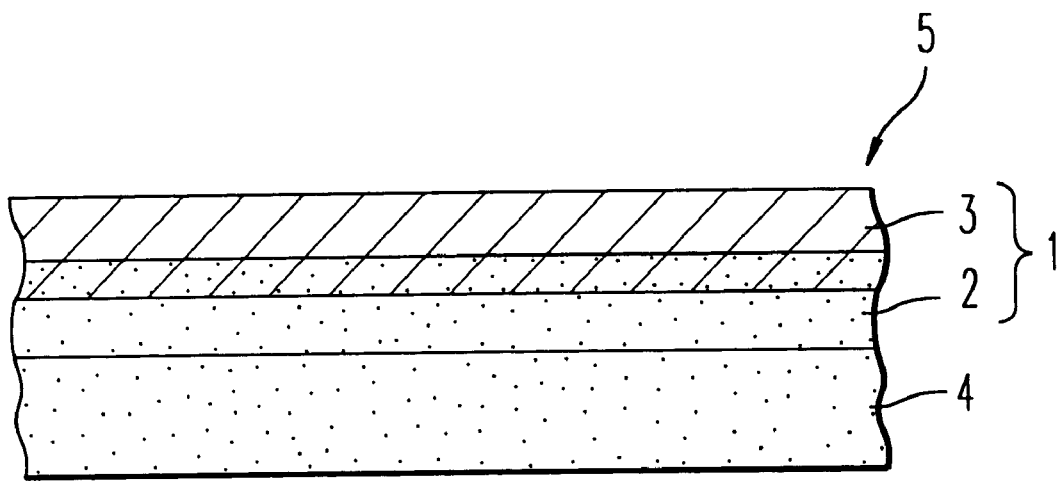
FIG. 1 is a cross sectional view schematically illustrating a sheet pack according to the present invention.

A sheet pack of the present invention includes a multi-layer moisture-permeable support having a hydrophobic layer and a hydrophilic layer. A cosmetic substance is contained in the hydrophilic layer of the multi-layer moisture-permeable support to form a film. The sheet pack of the present invention accordingly gives an excellent tensile strength to a resulting film, which is not easily torn in the course of peeling off and does not cause any remains of the film on the surface of a skin during peeling off. The sheet pack of the present invention has the hydrophobic layer of the multi-layer moisture-permeable support on its surface, which is accordingly not sticky. The multi-layer moisture-permeable support of the sheet pack has excellent moisture permeability. This effectively shortens the period of time required for drying the cosmetic substance applied to the skin. Especially, when the cosmetic substance has a film-forming property, the period of time necessitated for completing the formation of a film after the application of the sheet pack to the skin can be shortened.

Also, according to the method for applying the sheet pack to a skin of the present invention, after supplying moisture in the form of water or clear lotion to a specific site of the skin, the sheet pack is applied to the specific site. The cosmetic substance included in the sheet pack is accordingly dissolved in the moisture supplied to the skin to yield a solution having a low viscosity. This solution permeates through the texture and the pores of the skin. The sheet pack thus more closely adheres to the skin and improves the effects according to the present invention, especially keratotic removal effect.

Especially, when a cosmetic substance in dry state is included in the sheet pack, the period of time necessary for completing the formation of a film can be shortened after the application of the sheet pack to the skin.

As mentioned above, the sheet pack of the present invention includes the multi-layer moisture-permeable support having a hydrophobic layer and a hydrophilic layer, other than the cosmetic substance.

The multi-layer moisture-permeable support of the sheet pack typically has a double layer structure, that is, one hydrophobic layer and one hydrophilic layer. As one embodiment shown in FIG. 1, a cosmetic substance 4 is retained by a hydrophilic layer 2 of a multi-layer moisture-permeable support 1 composed of the hydrophilic layer 2 and a hydrophobic layer 3. In other words, the hydrophilic layer 2 is impregnated with the cosmetic substance 4. The hydrophobic layer 3 which is laminated on the hydrophilic layer 2 forms the surface of a sheet pack 5.

Figure 2:
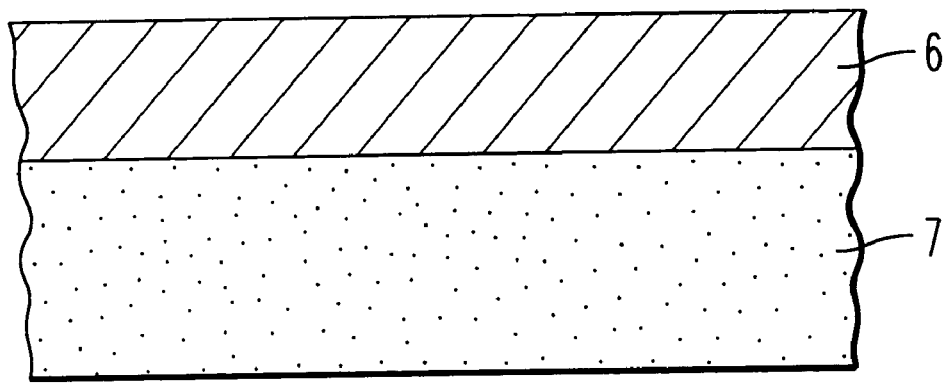
FIG. 2 is a cross sectional view schematically illustrating a conventional sheet pack.
Figure 3:
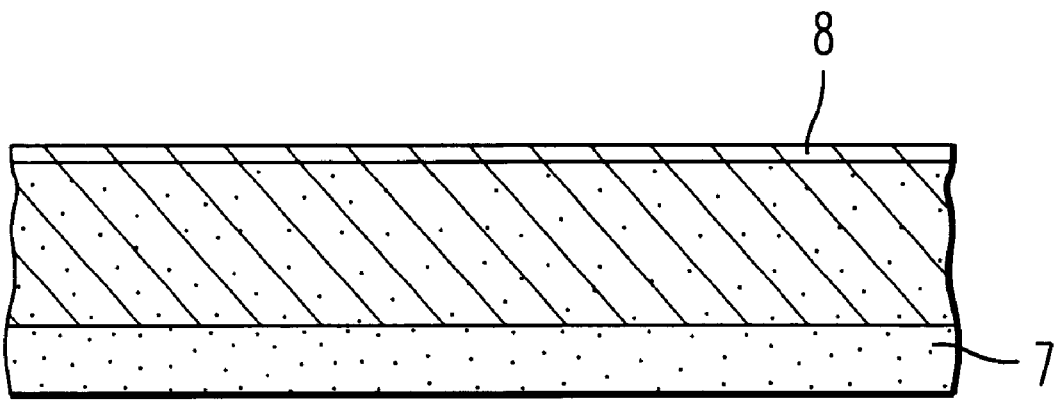
FIG. 3 is a cross sectional view schematically illustrating another conventional sheet pack.
Figure 4:
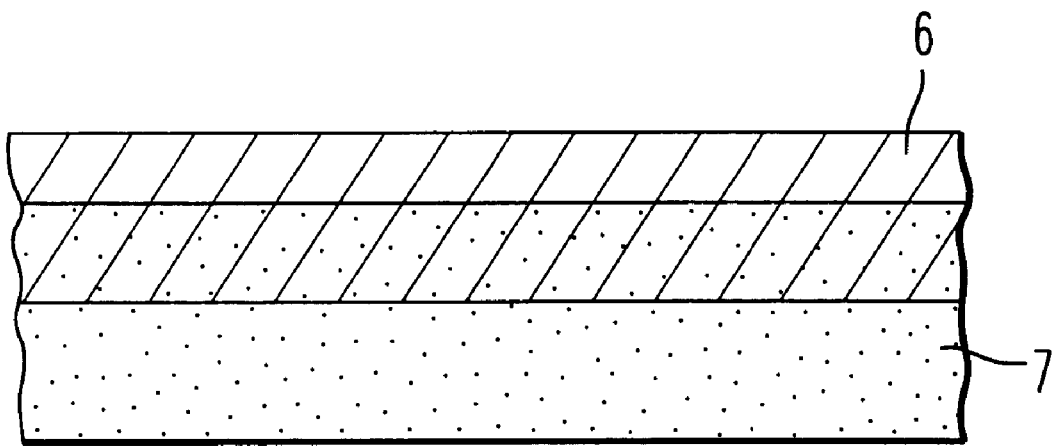
FIG. 4 is a cross sectional view schematically illustrating still another conventional sheet pack.

The structure of the multi-layer moisture-permeable support and the structure of the sheet pack including the multi-layer moisture-permeable support are significantly different from the structure of conventional sheet packs using a non-woven fabric as a support. The sheet pack of the present invention has a structure quite different from that of a conventional pack as shown in FIG. 2, wherein a hydrophobic support 6 is simply laid over a layer of a cosmetic substance 7, from that of another conventional pack as shown in FIG. 3, wherein a hydrophilic support 8 is impregnated with the cosmetic substance 7, and from that of still another conventional pack as shown in FIG. 4, wherein a hydrophobic support 6 is partly impregnated with the cosmetic substance.

In the present invention, as shown in FIG. 1, the multi-layer moisture-permeable support 1 has a hydrophobic layer 3 and a hydrophilic layer 2. The multi-layer moisture-pearmable support 1 is required to possess moisture permeability in order to dry the cosmetic substance or complete the formation of a film within a short period of time. The material applicable to the multi-layer moisture-permeable support 1 is, for example, a fabric or a laminate of a fabric and a film. It is not required that the hydrophobic layer 3 and the hydrophilic layer 2 are respectively composed of a single hydrophobic material and a single hydrophilic material. As long as the hydrophobic layer has hydrophobic property and the hydrophilic layer has hydrophilic property to exhibit sufficient affinity to the cosmetic substance, both the hydrophobic layer and the hydrophilic layer may be composed of a mixture of a hydrophobic material and a hydrophilic material.

The material used in the multi-layer moisture-permeable material may be treated to exhibit hydrophobic property or hydrophilic property as occasion demands. Also, the materials for the hydrophobic layer and the hydrophilic layer may be treated with a surface active agent selected from a fatty acid ester-type nonionic surface active agent, a polyglycerol fatty acid ester, an alkyl ether sulfate, a higher alcohol sulfate, a metal salt of alkylphosphate and mixtures thereof to give the material hydrophilic property as occasion demands.

When a fabric is used in the multi-layer moisture-pearmable support, the hydrophobic layer may be composed of a hydrophobic synthetic fiber made of a polymer such as polyester, polyethylene, polypropylene or polyurethane, or an inorganic fiber.

The hydrophilic layer may be composed of a hydrophilic fiber such as a natural fiber such as cotton, flax or wool, or a cellulose fiber such as rayon or acetate. As described in the above, a mixture of a hydrophilic fiber with a hydrophobic fiber made of a polymer such as polyester, polyethylene, polypropylene or polyurethane may be used in the present invention. The content of the hydrophilic fiber in the hydrophilic layer is preferably not less than 5% by weight, more preferably not less than 10% by weight. The hydrophilic layer may also be composed of the above hydrophobic fiber which is treated with a surface active agent selected from a metal salt of alkylphosphate, silicone compounds, acrylate compounds, fluorine-containing compounds and mixtures thereof to impart hydrophilic property to the hydrophobic fiber.

The preferable diameter of those fibers ranges several to 50 $\mu$m or so. In order to prevent the strike-through of the cosmetic substance and ensure the favorable hand feeling of the sheet pack, the diameter of not greater than 30 $\mu$m is more preferable. Twist yarns or spun yarns of filaments of 5 to 20 $\mu$m in diameter may also be used as the fibers.

Also, it is desired that the finess of the fiber is from about 0.01 to about 15 deniers, preferably from about 0.01 to about 3 deniers.

Textile fabrics, knitted fabrics, non-woven fabrics, and combinations thereof may be applicable to the fabric. Among them, non-woven fabrics are especially preferable from the viewpoints of the cost, productivity and hand feeling.

In case that a non-woven fabric is used as the hydrophilic layer, it is desired that the water-resistant pressure from the hydrophilic layer side of the multi-layer moisture-permeable support is preferably not less than 0.1 g/cm², more preferably not less than 0.2 g/cm², particularly not less than 2 g/cm², in order to prevent the strike-through of the cosmetic substance from the hydrophilic layer to the hydrophobic layer. The water-resistant pressure is measured by the following manner.

Figure 5:
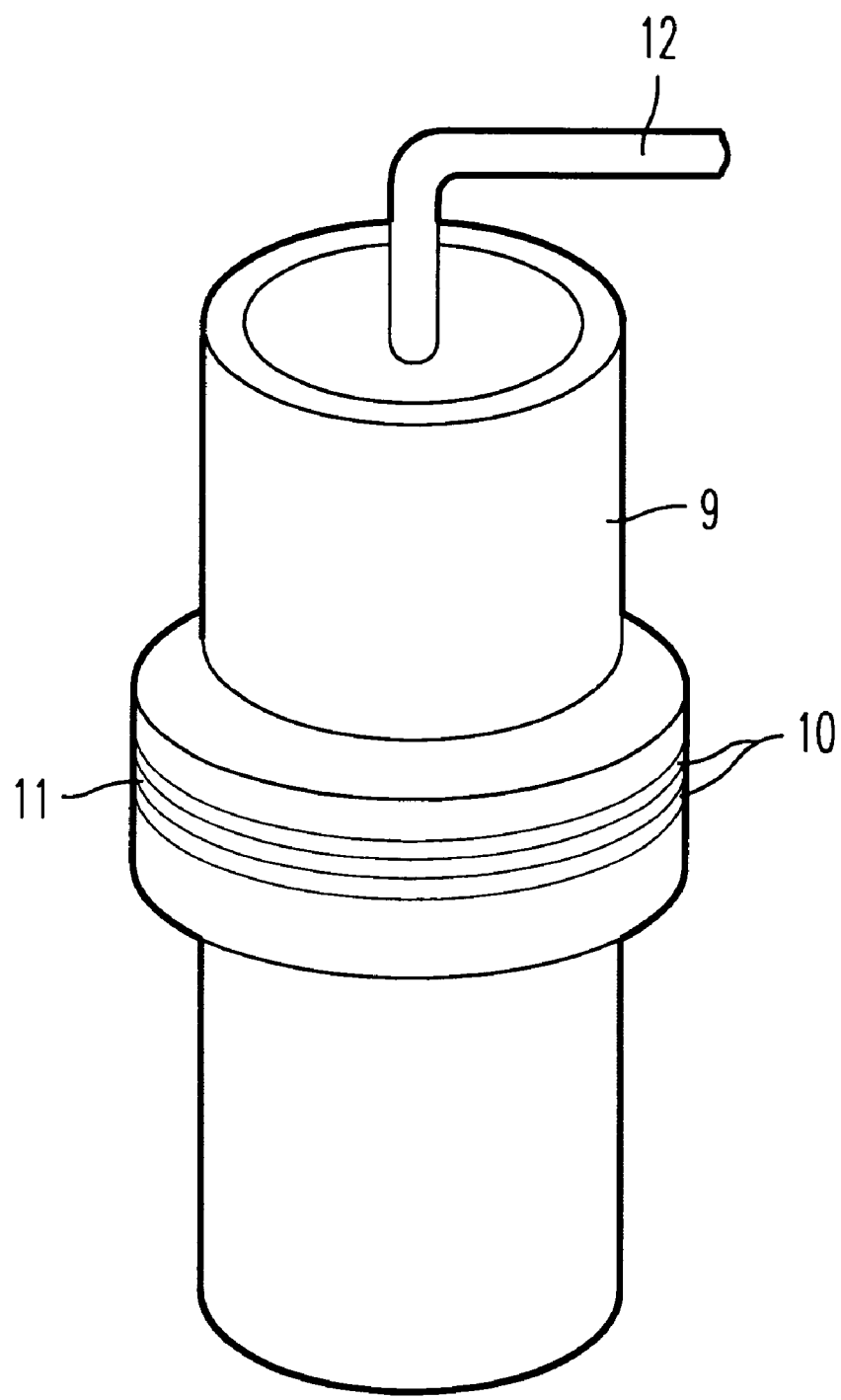
FIG. 5 is a schematic view showing a method for measuring a water-resistant pressure of a sheet pack.

As shown in FIG. 5, a non-woven fabric 11 is set in a cylindrical tube 9 having the sectional area of 9.6 cm² with a rubber packing 10, and ion-exchanged water 12 is poured from an inlet which is provided in the upper portion of the cylindrical tube 9 at a rate of 4 g per minute. The period of time in which ion-exchanged water passes through the non-woven fabric 11 to the bottom of the cylindrical tube 9 is measured, and the water-resistant pressure is calculated according to the equation given below: [Water-resistant pressure (g/cm²)]=[Period of time (seconds)]×(4 g/60 seconds)/9.6 cm²

The moisture permeability of the fabric depends upon the porosity. The lower porosity slows down the drying rate of the cosmetic substance and may cause contamination of the air in the process of manufacturing a sheet pack, especially at the time of impregnating a sheet fabric with the cosmetic substance. The higher porosity, on the other hand, lowers the mechanical strength of the resulting pack sheet and may cause the cosmetic substance to remain on the skin when the sheet pack is peeled off the skin. The porosity is thus preferably 70 to 99%, more preferably 85 to 99%. The porosity is represented by the following equation:

$$[\text{Porosity (\%)}]=(\rho-\rho')\times 100/\rho$$

wherein ρ is a specific gravity of the multi-layer moisture-permeable support, and ρ' is an apparent specific gravity of the multi-layer moisture-permeable support.

The smaller thickness of the hydrophilic layer lowers the retaining property of the cosmetic substance and the film strength, and may cause the cosmetic substance to remain on the skin when the sheet pack is peeled off the skin. The larger thickness of the hydrophilic layer, on the other hand, increases the amount of the cosmetic substance applied to the skin and lengthens the period of time necessary for drying the cosmetic substance or completing the formation of a film.

The extremely small thickness of the hydrophobic layer causes the cosmetic substance to leak through the hydrophobic layer and make its surface sticky when the sheet pack is applied to the skin. The extremely large thickness of the hydrophobic layer, on the other hand, prevents the resulting sheet pack from fitting the contour of the skin site.

When the hydrophilic layer and the hydrophobic layer are made of a fabric, respectively, it is desired that each layer has a thickness of 20 to 2000 μm, preferably 30 to 1500 μm, respectively.

Also, when the hydrophilic layer and the hydrophobic layer are made of a fabric, it is desired that the thickness of the whole multi-layer moisture-permeable support is preferably 40 to 2000 μm, more preferably 50 to 1500 μm, and that the area weight of the whole multi-layer moisture-permeable support is preferably 4 to 200 g/m², more preferably 5 to 150 g/m².

It is also preferable that the fabric has some stretching properties, in order to enable the sheet pack to fit the contour of the skin. The preferable elongation is not higher than 100% since the extremely large elongation lowers the film strength of the cosmetic substance and peel-off properties.

The elongation of the fabric depends upon its material. Fabrics having a preferable elongation include textile fabrics and knitted fabrics which are composed of fibers prepared by melt spinning or wet spinning styrene thermoplastic elastomers (TPE) such as styrene-isoprene-styrene elastomer (SIS), styrene-butadiene-styrene elastomer (SBS), styrene-ethylene-butadiene-styrene elastomer (SEBS) and styrene-ethylene-propylene-styrene elastomer (SEPS); olefin TPE, such as ethylene-propylene copolymer (EPM), ethylene-propylene-crosslinkable diene monomer (for example, ethylidene norbornene) terpolymer (EPDM); vinyl chloride TPE, urethane TPE, ester TPE, amide TPE, and other TPE, or twist yarns thereof, and textile fabrics and knitted fabrics which are composed of those fibers and other fibrous materials.

Applicable examples of the non-woven fabric include spun-bonded fabrics obtained by melt-blowing or spun-bonding the TPE, non-woven fabrics which are prepared by a spun lacing method or a water-jet method, and non-woven fabrics which are prepared by confounding core-sheath type conjugated fibers or side-by-side type conjugated fibers that include two different polymers selected from olefin resins, polyester resins, polyamide resins and other resins through a needle punch or spun lace process or by emboss-bonding those complex fibers with heat or ultrasonic waves, and then thermally shrunk (micro-crimped) with hot-air to give a textured structure.

The elongation and deformation of the fabric may be isotropic in all directions or otherwise anisotropic in a specific direction.

A variety of materials other than the fabrics mentioned above can be used in the multi-layer moisture-permeable support. In case that the fabric does not have a sufficient mechanical strength or that moisture permeability is adjusted, a laminate of a fabric and a film prepared by thermal lamination or bonding may be used as the multi-layer moisture-permeable support.

Possible materials for the film include diene polymers such as natural rubber, isoprene rubber and butadiene rubber; polyolefins such as polyethylene and polypropylene; polyamides such as nylon-66, nylon-6 and nylon-12, vinyl or vinylidene polymers such as polyvinyl chloride, polyvinylidene chloride, polystyrene, polyvinyl acetate, polyacrylonitrile and polymethyl methacrylate; polyesters such as polyethylene terephthalate and polybutylene terephthalate; ethylene copolymers such as ethylene-vinyl acetate copolymer, ethylene-acrylic acid copolymer and ethylene-acrylate copolymer; polyacetate, polyurethane, and modified or blended compounds thereof. Styrene thermoplastic TPE, such as SBS, SEBS and SEPS, olefin TPE such as EPM and EPDM, vinyl chloride TPE, urethane TPE, ester TPE, amide TPE and other TPE may also be used to enhance elongation.

A moisture-permeable film can be obtained from those film materials by any of the following methods: a process of kneading the above resin as a film material with an inorganic or organic filler in a molten state and molding it into a sheet, and elongating the sheet; a process of dispersing in the above resin a resin which is incompatible with the above resin in a molten state in place of the above filler, and molding it into a sheet and stretching the sheet to give a moisture-permeable sheet; a process of kneading the above resin as a film material with an oily component in a molten state in place of the filler, and molding it into a sheet and stretching the sheet to give a moisture-permeable sheet; a process of kneading the above resin as a film material with an oily component or a wax component, molding it into a sheet and extracting the oily or wax component for its removal; a process of sintering the above resin as a film material; and a process of molding the above resin as a film material into a sheet and forming pores in the sheet by electrical discharge machining. A foamed sheet of the above resin, and a thermoplastic elastomer sheet which is obtained by molding a mixture of a thermoplastic elastomer with a water-soluble substance, a salt and polyvinyl alcohol into a sheet and extracting the additives including the water-soluble substance from the sheet are also possible examples of the moisture-permeable film. Other available examples are moisture-permeable resin sheets made of urethane elastomer, ester elastomer, polyvinyl alcohol or cellophane. When a sheet having substantially no moisture-permeability is used, a number of very small through holes can be formed in the film to give moisture-permeability.

The moisture-permeability of the film can be measured in accordance with the measuring method prescribed in JIS Z0208. In order to prevent the strike-through of the cosmetic substance and ensure the favorable hand feeling, it is desired that the moisture-permeability is not more than 10000 $g/m^2$/24hours. Also, in order to improve the drying rate of the cosmetic substance, it is desired that the moisture-pemeability is not less than 100 $g/m^2$/24hours.

The extremely small thickness of the film lowers the improving effect of film strength and may tear the film and cause the cosmetic substance to remain on the skin when the sheet pack is peeled off the skin. The extremely large thickness of the film, on the other hand, prevents the resulting sheet pack from fitting the contour of the skin and undesirably increases the manufacturing cost. The preferable thickness of the film is usually 20 to 50 µm or so.

Known methods are applicable to the lamination of a fabric and a film. For example, there can be employed a process of thermally laminating a fabric and a resin film which has previously been dissolved in a solvent or thermally molten, a hot melt process of bonding a film to a fabric by a hot melt adhesive agent; and a process of bonding a film to a fabric with ultrasonic waves or by heat embossing.

Available examples of the cosmetic substance include a variety of film-forming cosmetic substances conventionally used for the peel-off type packs and water-containing gel cosmetic substances used for cataplasms. The cosmetic substance may be in a paste-like state containing sufficient moisture or in a dry state. In the latter case, moisture is added to the cosmetic substance before its use.

A film-forming agent included in the film-forming cosmetic substance may be, for instance, polyvinyl alcohol, polyvinyl pyrrolidone, polyvinyl acetate emulsion or carboxymethylcellulose. A thickening agent included in the film-forming cosmetic substance may be pectin, gelatin, xanthan gum, carrageenan, sodium alginate, pullulan, methylcellulose, hydroxyethylcellulose, hydroxypropylcellulose or carboxyvinyl polymer.

The film-forming cosmetic substance may contain various components such as an ingredient for moisture retention, an ingredient for absorption of sebum or an ingredient for removal of keratotic plug in accordance with its use.

In case that the film-forming cosmetic substance is an ingredient for moisture retention, for example, a humectant can be included in the film-forming cosmetic substance. Available examples of the humectant include, for instance, ethlene glycol, polyethylene glycols such as diethlene glycol and triethlene glycol; propylene glycol, polypropylene glycols such as dipropylene glycol, butylene glycols such as 1,3-butylene glycol and 1,4-butylene glycol; glycerol, polyglycerols such as diglycerol, sugar alcohols such as sorbitol, mannitol, xylitol and maltitol, monosaccharides such as galactose, glucose and fructose, and polysaccharides such as maltose and lactose. Possible examples of the oil component (emollient component) include hydrocarbons such as liquid parafiin, squalane and solid paraffin, natural oils such as olive oil, jojoba oil, evening primrose oil, palm oil and cow oil, esters such as isopropyl myristate, cetyl isoctanoate and neopentylglycol dicaprate, silicone oils such as methl polysiloxane, methyl polycyclosiloxane and methylphenyl polysiloxane, higher fattyacids such as isostearic acid and oleic acid.

In case that the film-forming cosmetic substance is an ingredient for absorption of sebum, for example, sebum absorbent can be included in the film-forming cosmetic substance. Available examples of the sebum absorbent include, for instance, kaolin, clay, bentonite, calcium carbonate, titanium dioxide, zinic oxide and silica.

In case that the film-forming cosmetic substance is an ingredient for removal of keratotic plug, it is preferable to use a polymer having an anionic, cationic or amphoteric salt-forming group as disclosed in Japanese Patent Laid-Open No. 5-97627 as a film forming agent, in order to form a film having a high film strength and enable the keratotic plug of the skin to be taken into the film for removal. More concretely, it is desired that the polymer has a salt-forming group such as carboxyl group, a sulfonate residual group, a sulfate residual group, a phosphate residual group, a nitrate residual group, amino group or ammonium group. Among them, as the film-forming agent, polymethacryloyloxyethyltrimethylammonium chloride can be especially preferably used.

The cosmetic substances further may include a variety of components which are generally used for the cosmetic substance, for example, a whitening component such as vitamin C or placenta extract, antiphlogistic components such as a glycyrrhetinic acid salt, a coloring agent such as a pigment, a surface active agent, an antiseptic agent and a sterilizing agent.

The amount of the cosmetic substance cannot be absolutely determined because the amount varies depending upon the kind of the multi-layer moisture-pemeable support, and the like. It is desired that the amount is usually 5 to 2000 $g/m^2$, preferably 10 to 1000 $g/m^2$.

The sheet pack of the present invention includes the cosmetic substance and the multi-layer moisture-permeable support as described above. A release sheet which can be peeled off in use may also be laid over the cosmetic-substance-containing surface as occasion demands. As the release sheet, there can be used a resin sheet made of polyester, polypropylene, polyethylene, nylon, and the like.

The sheet pack of the present invention may have any outer shape. For example, the sheet pack of the present invention may have a predetermined width and be cut to an appropriate size in application to the skin. The sheet pack may alternatively be cut in advance to the shape suitable for the whole face pack or the partial face pack, for example, for forehead, cheek or nose.

For instance, as shown in FIG. 6(*a*), when the sheet pack 5 has a substantially triangular shape, the sheet pack 5 can be suitably used for the nose as shown in FIG. 6(*b*).

As shown in FIG. 7(*a*), when the sheet pack 5 has a substantially T shape, the sheet pack 5 can be suitably used for the T zone of the face as shown in FIG. 7(*b*).

Also, as shown in FIG. 8(*a*), when the sheet pack 5 has a substantially U shape, the sheet pack 5 can be suitably used for the U zone of the face as shown in FIG. 8(*b*).

One embodiment of a preferable method for manufacturing the sheet pack of the present invention is as follows: The constituents of the cosmetic substance are homogeneously stirred, and water is added thereto to adjust its viscosity, to give a liquid cosmetic substance. In this case, it is preferable that the content of water is 10 to 95% by weight. Thereafter, the liquid cosmetic substance is uniformly spread over a release sheet with an applicator, and the multi-layer moisture-permeable support is laminated on the release sheet, so as to impregnate the hydrophilic layer of the multi-layer moisture-permeable support with the cosmetic substance. In case that the liquid cosmetic substance has a low viscosity, the hydrophilic layer is naturally impregnated with the cosmetic substance. In case that the liquid cosmetic substance has a high viscosity, ample time can be taken for the impregnation. Alternatively, after the release sheet is coated with the liquid cosmetic substance, a multi-layer moisture-permeable support is laminated on the coated surface, and the multi-layer moisture-permeable support is pressed toward the release sheet with a roller.

In case that the sheet pack has a pasty cosmetic substance, the sheet pack is cut to an appropriate shape after the adjustment of its water content, and sealed in a package bag or a case having no moisture permeability, in order to prevent the moisture from being lost from the sheet pack before application to the skin. In case that the cosmetic substance is in a dry state, on the other hand, the sheet pack is cut to an appropriate shape after the cosmetic substance is dried. The drying process can be carried out by allowing the sheet pack to stand for several hours at room temperature or raised temperature.

The sheet pack including the cosmetic substance in a paste-like state generally has a water content of 30 to 80% by weight and a thickness of 50 to 2000 μm, whereas the sheet pack including the cosmetic substance in a dry state generally has a water content of 0.1 to 30% by weight and a thickness of 10 to 1000 μm.

In case that the sheet pack of the present invention includes the cosmetic substance in a paste-like state, the surface of the hydrophilic layer containing the cosmetic substance can be directly applied to a skin and peeled off the skin after the cosmetic substance is dried or the formation of a film is completed.

In case that the sheet pack includes the cosmetic substance in a dry state, water or clear lotion is supplied to the surface of the hydrophilic layer containing the cosmetic substance or the skin to be contacted with the sheet pack. Thereafter, in the same manner as the above, the surface of the hydrophilic layer containing the cosmetic substance is applied to the skin, and the sheet pack is peeled off the skin after the cosmetic substance is dried or the formation of a film is completed.

Irrespective of whether the cosmetic substance is in a paste-like state or in a dry state, it is preferable in the present invention that moisture such as water or clear lotion is supplied to the skin site before the application of the sheet pack to the skin. The cosmetic substance included in the sheet pack is accordingly dissolved in the moisture which is supplied to the skin, and a solution having a low viscosity is generated. This solution permeates through the texture and pores of the skin. The sheet pack thus closely adheres to the skin and improves the effects according to the present invention, especially keratotic removal effect.

In case that the cosmetic substance is in a dry state, this procedure enables the sheet pack to be applied to the skin with a minimum amount of moisture. This effectively shortens the period of time required for drying the cosmetic substance or completing the formation of a film.

The present invention is described more concretely according to some examples.

EXAMPLE 1

(1) Manufacture of sheet pack

A double-layer non-woven fabric (area weight: 25 g/m$^2$, porosity: 92%) was prepared as a multi-layer permeable support by bonding a hydrophobic web (area weight: 15 g/m$^2$, thickness: 0.18 mm) composed of polypropylene fibers as a hydrophobic layer, to a hydrophilic web (area weight: 10 g/m$^2$, thickness: 0.12 mm) composed of 40% by weight of polypropylene fibers and 60% by weight of rayon fibers as a hydrophilic layer by means of a heat embossing process. The water-resistant pressure of the non-woven fabric from the hydrophilic layer side was 2 to 3 g/cm$^2$.

A mixture of 25.0% by weight of polymethacryloyloxyethyltrimethylammonium chloride, 5.0% by weight of polyvinyl alcohol, 5.0% by weight of glycerol, 10.0% by weight of ethanol, 0.2% by weight of polyoxyethylene-hardened castor oil, 0.1% by weight of methyl paraben, a trace amount of a perfume and 54.7% by weight of purified water was stirred at room temperature with a stirrer. The solution was deaerated under reduced pressure to give a film-forming cosmetic solution for removal of keratotic plug.

The film-forming cosmetic solution was homogeneously flown and spread over a release sheet made of a polypropylene film to have a thickness of approximately 300 μm (amount: about 300 g/m$^2$). Immediately after that, the surface of the hydrophilic layer of the multi-layer moisture-permeable support prepared in the above was laminated on the film-forming cosmetic solution-coated surface of the release sheet. The laminate was placed in a hot-air dryer of 80° C. for removal of moisture. This procedure gave a sheet pack 5 as shown in FIG. 1, wherein only the hydrophilic layer 2 of the multi-layer moisture-permeable support 1 was impregnated with the film-forming cosmetic substance 4 and the hydrophobic layer 3 formed a surface layer. The water content of the film-forming cosmetic substance was 17 to 19% by weight.

(2) Evaluation of sheet pack

The sheet pack obtained was subjected to the use-test by a panel.

Figure 6A:
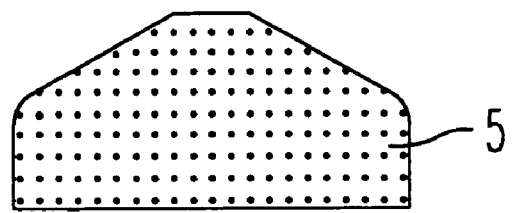
FIG. 6 is a schematic view showing a sheet pack in a substantially triangular shape according to the present invention and one embodiment thereof.
Figure 6B:
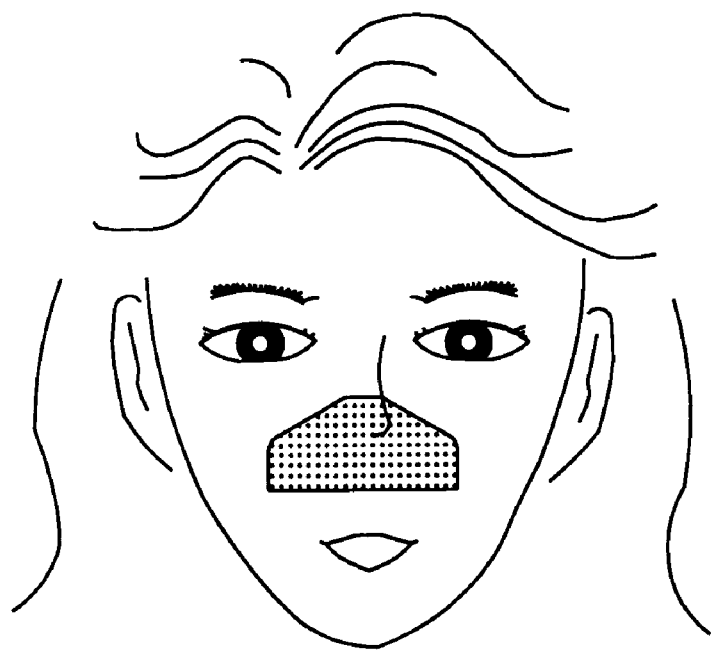

In the use-test, the sheet pack was cut in advance to the nose shape as shown in FIG. 6(a). An appropriate amount of water was supplied to the specific skin site to which the sheet pack was applied, and the sheet pack of the nose shape was then pressed against the specific skin site as shown in FIG. 6(b). The sheet pack was peeled off the skin after being dried. The panel evaluated the sheet pack for the stickiness of surface, adhesion, drying properties, peel-off properties, remains of the peel, removal effect of keratotic plug and greasy smoothness of skin by the following criteria for evaluation.

The results of evaluation are shown in Table 1.

[Criteria for evaluation]

(A) Stickiness of surface

⊚: Stickiness is entirely nothing.

○: Stickiness is almost nothing.

Δ: Stickiness is a little generated.

×: Stickiness is distinctly generated.

(B) Adhesion

⊚: Complete adhesion is observed.

○: Almost complete adhesion is observed.

Δ: Insufficient adhesion is observed.

×: No adhesion is observed.

(C) Drying properties

⊚: Cosmetic substance is dried in a very short period of time.

○: Cosmetic substance is dried in a relatively short period of time.

Δ: Cosmetic substance is dried in a relatively long period of time.

x: Cosmetic substance is dried in a very long period of time.

(D) Peel-off properties

⊚: Peeling-off is very easy.

○: Peeling-off is easy.

Δ: Peeling-off is difficult.

x: Peeling-off is very difficult.

(E) Remains of the peel

⊚: No remains of the peel are entirely observed.

○: Almost no remains of the peel are observed.

Δ: Slight remains are observed.

x: Many remains are observed.

(F) Removal effect of keratotic plug

⊚: Very high

○: High

Δ: Low x: Very low (G) Greasy smoothness

⊚: Very smooth

○: Smooth

Δ: A little smooth x: No change is observed.

EXAMPLE 2

A sheet pack (water content: 17 to 19% by weight) was manufactured in the same manner as Example 1, except that a double-layer non-woven fabric (area weight: 25 g/m$^2$, water-resistant pressure from the hydrophilic layer side: 0.15 g/cm$^2$, porosity: 94%) was prepared by bonding a non-woven fabric (area weight: 12 g/m$^2$) composed of core(polyester)-sheath(polyethylene) conjugated fibers, which were treated with a water-repellent oil reagent as a hydrophobic layer, to a non-woven fabric (area weight: 13 g/m$^2$) composed of the above conjugated fibers, which were treated with a hydrophilic oil reagent as a hydrophilic layer by means of ultrasonic waves.

The sheet pack thus obtained was evaluated in the same manner as in Example 1.

The results of evaluation are shown in Table 1.

EXAMPLE 3

The sheet pack was prepared in the same manner as Example 1 and subsequently evaluated. In the use-test of Example 3, an appropriate amount of water was not supplied to the specific skin site but was spread over the application surface of the sheet pack before the sheet pack was applied to the nose.

The sheet pack was peeled off the skin after being dried.

The results of evaluation are shown in Table 1.

COMPARATIVE EXAMPLE 1

A sheet pack (water content: 17 to 19% by weight) was manufactured in the same manner as in Example 1, except that a hydrophobic single-layer non-woven fabric (area weight: 22 g/m$^2$, water-resistant pressure: 4.1 g/cm$^2$, porosity: 91%) composed of core(polyester)-sheath(polyethylene) conjugated fibers, which was manufactured by spun bonding, was used as a moisture-permeable support.

The sheet pack thus obtained was evaluated in the same manner as in Example 1.

The results of evaluation are shown in Table 1.

COMPARATIVE EXAMPLE 2

A sheet pack (water content: 17 to 19% by weight) was manufactured in the same manner as in Example 1, except that a hydrophilic single-layer non-woven fabric (area weight: 22 g/m$^2$, water-resistant pressure: 4.1 g/cm$^2$, porosity: 93%) composed of core(polyester)-sheath(polyethylene) conjugated fibers, which was manufactured by spun bonding and treated with a hydrophilic oil reagent, was used as a moisture-permeable support.

The sheet pack thus obtained was evaluated in the same manner as in Example 1.

The results of evaluation are shown in Table 1.

COMPARATIVE EXAMPLE 3

A sheet pack (water content: 17 to 19% by weight) was manufactured in the same manner as in Example 1, except that a hydrophobic single-layer non-woven fabric (area weight: 22 g/m$^2$, water-resistant pressure: 4.1 g/cm$^2$, porosity: 93%) composed of 40% by weight of polypropylene fibers and 60% by weight of rayon fibers, which was manufactured by means of a heat embossing process, was used as a moisture-permeable support.

The sheet pack thus obtained was evaluated in the same manner as in Example 1.

The results of evaluation are shown in Table 1.

COMPARATIVE EXAMPLE 4

A sheet pack (water content: 17 to 19% by weight) was manufactured in the same manner as in Example 1, except that a hydrophobic single-layer non-woven fabric (area weight: 22 g/m$^2$, water-resistant pressure: 4.1 g/cm$^2$, porosity: 93%) composed of core(polyester)-sheath(polyethylene) conjugated fibers, which was manufactured by spun bonding, was used as a moisture-permeable support, and that the non-woven fabric was impregnated with a film-forming cosmetic substance by stretching a laminate of the permeable support laid upon the layer of the film-forming cosmetic substance with rollers.

The sheet pack thus obtained was evaluated in the same manner as in Example 1.

The results of evaluation are shown in Table 1.

TABLE 1

| | Results of evaluation | | | | | | |
|---|---|---|---|---|---|---|---|
| | Stickiness of surface | Adhesion | Drying Properties | Peel-off Properties | Remains of the peel | Removal effect of keratotic plug | Greasy smoothness of skin |
| Example No. | | | | | | | |
| 1 | ⊙ | ⊙ | ⊙ | ⊙ | ⊙ | ⊙ | ⊙ |
| 2 | ⊙ | ⊙ | ⊙ | ⊙ | ○ | ⊙ | ⊙ |
| 3 | ○ | ⊙ | △ | ○ | ⊙ | ⊙ | ⊙ |
| Com. Ex. | | | | | | | |
| 1 | ⊙ | ⊙ | ⊙ | X | X | △ | △ |
| 2 | X | ⊙ | ⊙ | △ | ⊙ | ⊙ | ⊙ |
| 3 | X | ⊙ | ⊙ | △ | ⊙ | ⊙ | ⊙ |
| 4 | △ | ⊙ | ⊙ | X | X | △ | △ |

EXAMPLE 4

A sheet pack was manufactured in the same manner as in Example 1, except that as a film-forming cosmetic substance for moisture retention, there was used a mixture of 8.0% by weight of polyvinyl alcohol, 5.0% by weight of squalane, 5.0% by weight of dipropylene glycol, 5.0% by weight of glycerol, 10.0% by weight of ethanol, 0.2% by weight of polyoxyethylene hardened castor oil, 0.1% by weight of methyl paraben and 66.7% by weight of purified water.

The sheet pack obtained was subjected to the use-test by a panel for evaluation.

Figure 7A:
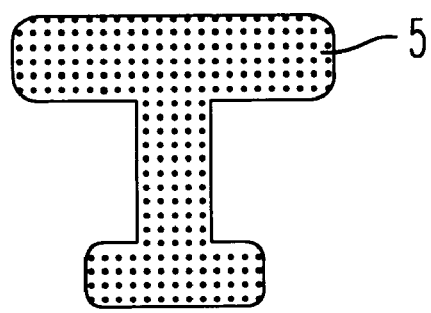
FIG. 7 is a schematic view showing a T-zone sheet pack according to the present invention and one embodiment thereof.
Figure 7B:
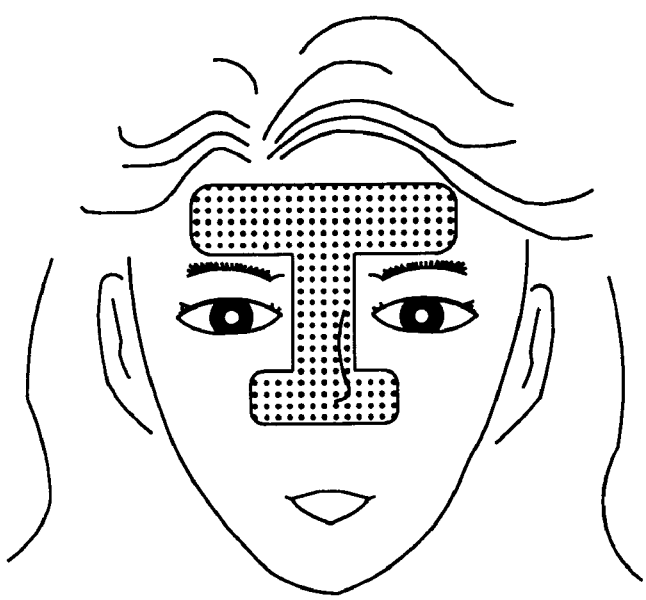
Figure 8A:
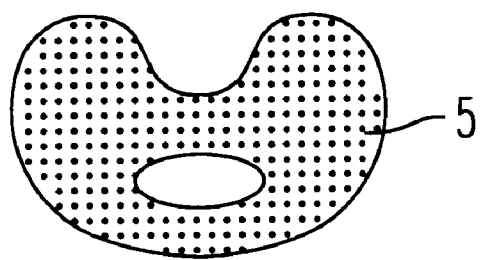
FIG. 8 is a schematic view showing a U-zone sheet pack according to the present invention and one embodiment thereof.
Figure 8B:
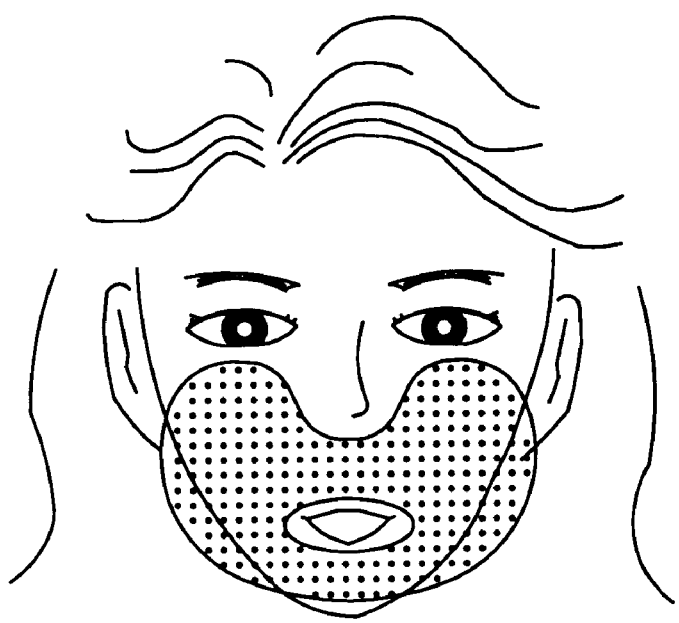

In the use-test, the sheet pack was cut in advance to a T-zone shape or to a U-zone shape as shown in FIG. 7(a) or 8(a). An appropriate amount of water was supplied to the specific skin site to which the sheet pack was applied, and the sheet pack having a T-zone shape or a U-zone shape was then pressed against the specific skin site as shown in FIG. 7(b) or 8(b). The sheet pack was peeled off the skin after being dried. The panel evaluated the sheet pack for the stickiness of surface, adhesion, drying properties, peel-off properties and remains of the peel in the same manner as in Example 1, and wetness of skin and smoothness of skin in accordance with the following criteria for evaluation.

The results of evaluation are shown in Table 2.

[Criteria for evaluation]

(H) Wetness of skin
⊙: Sufficiently wet
○: Wet
△: A little wet
x: No change of wetness is observed.

(I) Smoothness of skin
⊙: Very smooth
○: Smooth
△: A little smooth
x: No change of smoothness is observed.

EXAMPLE 5

A sheet pack was prepared in the same manner as in Example 1, except that the film-forming cosmetic substance was prepared in the same manner as in Example 4 and that the same double-layer non-woven fabric as used in Example 2 was used as a multi-layer permeable support.

The sheet pack thus obtained was evaluated in the same manner as in Example 4.

The results of evaluation are shown in Table 2.

EXAMPLE 6

The sheet pack was prepared in the same manner as in Example 4 and subsequently evaluated.

In the use-test of Example 6, an appropriate amount of water was not supplied to the specific skin site but was spread over the application surface of the sheet pack before the sheet pack was applied to the specific skin site. The sheet pack was peeled off the skin after being dried.

The results of evaluation are shown in Table 2.

EXAMPLE 7

A sheet pack was prepared in the same manner as in Example 1, except that the film-forming cosmetic substance was prepared in the same manner as in Example 4, and that a double-layer support (area weight: 45 g/m$^2$) which was manufactured by bonding a film (area weight: 35 g/m$^2$) made of straight-chain low-density polyethylene (L-LDPE), calcium carbonate and additives as a hydrophobic layer to a non-woven fabric (area weight: 10 g/m$^2$) composed of 40% by weight of polypropylene fibers and 60% by weight of rayon fibers as a hydrophilic layer by a heat embossing process was used as a multi-layer moisture permeable support. The water-resistant pressure of the double-layer support from the hydrophilic layer side was not less than 10 g/cm$^2$. The moisture permeability was 3600 to 4800 g/m$^2$/24 hours.

The sheet pack thus obtained was evaluated in the same manner as in Example 4.

The results of evaluation are shown in Table 2.

COMPARATIVE EXAMPLE 5

A sheet pack was prepared in the same manner as in Example 1, except that the same film-forming cosmetic substance as used in Example 3 was used, and that the same single-layer non-woven fabric as used in Comparative Example 1 was used as a permeable support.

The sheet pack thus obtained was evaluated in the same manner as in Example 4.

The results of evaluation are shown in Table 2.

COMPARATIVE EXAMPLE 6

A sheet pack was prepared in the same manner as in Example 1, except that the same film-forming cosmetic substance as used in Example 3 was used, and that the same single-layer non-woven fabric as used in Comparative Example 2 was used as a permeable support.

The sheet pack thus obtained was evaluated in the same manner as in Example 4.

The results of evaluation are shown in Table 2.

COMPARATIVE EXAMPLE 7

A sheet pack was prepared in the same manner as in Example 1, except that the same film-forming cosmetic substance as used in Example 3 was used, and that the same single-layer non-woven fabric as used in Comparative Example 3 was used as a permeable support.

The sheet pack thus obtained was evaluated in the same manner as in Example 4.

The results of evaluation are shown in Table 2.

TABLE 2

| | Results of evaluation | | | | | | |
|---|---|---|---|---|---|---|---|
| | Stickiness of surface | Adhesion | Drying Properties | Peel-off Properties | Remains of the peel | Wetness of skin | Smoothness of skin |
| Example No. | | | | | | | |
| 4 | ⊙ | ⊙ | ⊙ | ⊙ | ⊙ | ⊙ | ⊙ |
| 5 | ⊙ | ⊙ | ⊙ | ⊙ | ○ | ⊙ | ⊙ |
| 6 | ○ | ⊙ | △ | ⊙ | ⊙ | ⊙ | ⊙ |
| 7 | ⊙ | ⊙ | △ | ⊙ | ⊙ | ⊙ | ⊙ |
| Com. Ex. | | | | | | | |
| 5 | ⊙ | ⊙ | ⊙ | X | X | ⊙ | ⊙ |
| 6 | X | ⊙ | ⊙ | △ | ○ | ⊙ | ⊙ |
| 7 | X | ⊙ | ⊙ | △ | ⊙ | ⊙ | ⊙ |

As is clear from the results shown in Tables 1 and 2, it can be seen that the sheet packs having the double-layer support including a hydrophobic layer and a hydrophilic layer obtained in Examples 1 to 7 exhibit favorable results for the evaluation items, that is, stickiness of surface, adhesion, drying properties, peel-off properties, remains of the peel and beauty pack effects (removal effect of keratotic plug, greasy smoothness of the skin, wetness of skin, and smoothness of skin).

Compared with the methods of supplying moisture to the sheet pack, it can be seen that the method of supplying an appropriate amount of water to the specific skin site before the application of the sheet pack to the skin shows less stickiness of the surface and accelerates the drying process.

In Comparative Examples 1, 4 and 5 using a hydrophobic single-layer as a moisture-permeable support instead of a double-layer support including a hydrophobic layer and a hydrophilic layer, it can be seen that the sheet packs are not easily peeled off the skin and partly remained on the skin. In Comparative Examples 2, 3, 6 and 7 using a hydrophilic single layer, it can be seen that the sheet packs have sticky surface and are not easily handled.

The present invention being thus described, it will be obvious that the same may be varied in many ways. Such variations are not to be regarded as a departure from the spirit and scope of the invention, and all such modification as would be obvious to one skilled in the art are intended to be included within the scope of the claims.

INDUSTRIAL APPLICABILITY

The peel-off-type sheet pack of the present invention does not have a sticky surface, shortens the period of time required for drying a cosmetic substance or completing the formation of a film, is not easily torn in the course of peeling, and does not cause remains of the peeled-off film on the surface of the skin.

The method for applying the sheet pack to the skin of the present invention enhances keratotic removal effects shortens the period of time required for drying the cosmetic substance or completing the formation of a film after the application of the sheet pack to the skin.

What is claimed is:

1. A peel-off sheet pack comprising:
   i) a multi-layer moisture-permeable support having a hydrophobic layer bonded to a hydrophilic layer; and
   ii) a cosmetic substance,
   wherein said hydrophilic layer is impregnated with said cosmetic substance.

2. The sheet pack of claim 1, wherein said hydrophobic layer forms the surface of the sheet pack.

3. The sheet pack of claim 1, wherein said cosmetic substance is a film-forming cosmetic substance.

4. The sheet pack of claim 3, wherein said film-forming cosmetic substance comprises an ingredient for moisture retention, an ingredient for absorption of sebum or an ingredient for removal of keratotic plug.

5. The sheet pack of claim 4, wherein said ingredient for removal of keratotic plug is a polymer having a salt-forming group selected from the group consisting of carboxyl group, a sulfonate residual group, a sulfate residual group, a phosphate residual group, a nitrate residual group, amino group and ammonium group.

6. The sheet pack of claim 4, wherein said ingredient for removal of keratotic plug is polymethacryloyloxyethyltrimethyl ammonium chloride.

7. The sheet pack of claim 1, wherein each of the hydrophobic layer and the hydrophilic layer comprises a non-woven fabric, respectively.

8. The sheet pack of claim 7, wherein the water-resistant pressure of said non-woven fabric from the hydrophilic layer side is not less than 0.1 g/cm$^2$.

9. The sheet pack of claim 1, wherein the material used in said hydrophilic layer is treated with a surface active agent.

10. The sheet pack of claim 1, wherein said hydrophobic layer comprises a hydrophobic synthetic fiber made of polyethylene, polypropylene or polyester.

11. The sheet pack of claim 1, wherein said hydrophilic layer comprises rayon or cotton.

12. The sheet pack of claim 1, wherein said multi-layer moisture-permeable support is a laminate of a non-woven fabric and a moisture-permeable film.

13. A method for applying the sheet pack of claim 1, comprising the steps of:
   (A) supplying moisture to skin, and
   (B) applying the sheet pack to the moisture-supplied skin.

14. The method of claim 13, further comprising:
   C) allowing said cosmetic substance to dry; and
   D) peeling off said sheet pack from said skin.

* * * * *